United States Patent [19]

Chikama

[11] Patent Number: 5,363,882
[45] Date of Patent: Nov. 15, 1994

[54] BENDING DEVICE HAVING A BELLOWS

[75] Inventor: Toshio Chikama, Tokyo, Japan

[73] Assignee: Kabushiki Kaisha Machida Seisakusho, Tokyo, Japan

[21] Appl. No.: 37,559

[22] Filed: Mar. 26, 1993

Related U.S. Application Data

[62] Division of Ser. No. 594,118, Oct. 9, 1990, Pat. No. 5,203,380.

[30] Foreign Application Priority Data

Oct. 13, 1989 [JP] Japan .................. 1-264960
Oct. 13, 1989 [JP] Japan .................. 1-264961

[51] Int. Cl.$^5$ .................................. F16L 11/00
[52] U.S. Cl. ........................ 138/118; 138/103; 138/106; 138/119; 138/122; 138/172; 138/178; 138/DIG. 8; 128/4; 604/282
[58] Field of Search ............. 138/103, 110, 118, 121, 138/122, DIG. 8, 106, 119, 172, 178; 128/4; 604/282

[56] References Cited

U.S. PATENT DOCUMENTS

| | | | |
|---|---|---|---|
| 3,162,214 | 12/1964 | Bazinet | 138/120 |
| 3,739,770 | 6/1973 | Mori | 138/130 |
| 3,957,084 | 5/1976 | Jung | 138/122 |
| 4,826,087 | 5/1989 | Chinery | 128/4 |
| 4,942,905 | 7/1990 | Takemae et al. | 138/DIG. 8 |
| 5,143,475 | 9/1992 | Chikama | 128/4 |
| 5,176,126 | 1/1993 | Chikama | 138/120 |

FOREIGN PATENT DOCUMENTS

2028964 3/1980 United Kingdom ......... 138/DIG. 8

*Primary Examiner*—James E. Bryant, III
*Attorney, Agent, or Firm*—Fish & Richardson

[57] ABSTRACT

A bending device for use in an endoscope, a catheter or the like is of a simple construction having a coil, an operating wire and a pair of limitation members for limiting an axial compression of the coil. The pair of limitation members are arranged along the length of the coil, and are mounted respectively on diametrically-opposite portions of the coil. The coil is bendable in a direction perpendicular to a plane in which the pair of limitation members are disposed. Instead of the coil, a bellows can be used.

3 Claims, 5 Drawing Sheets

BENDING DEVICE HAVING A BELLOWS

This application is a division of U.S. application Ser. No. 07/594,118, filed Oct. 9, 1990, now U.S. Pat. No. 5,203,380.

BACKGROUND OF THE INVENTION

This invention relates to a bending device for use, for example, in an endoscope.

As is well known, an endoscope comprises a hollow body, a flexible insertion portion extending from a front end of the body, a flexible bending portion extending from a distal end of the insertion portion, and a rigid portion provided at a distal end of the bending portion. An inspection window and an illumination window are formed at the rigid portion.

Figure 1:
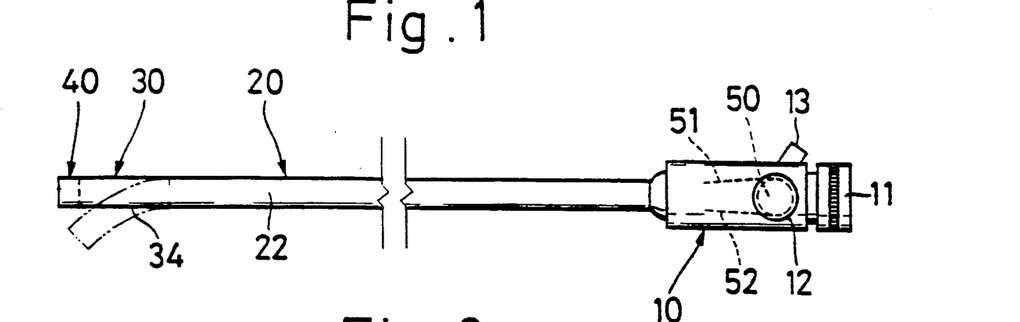
FIG. 1 is a schematic view of an endoscope incorporating a bending portion according to the present invention.

Japanese Utility Model Publication No. 9274/77 discloses a flexible tube structure for an endoscope which structure has one coil and a resilient thin plate. FIG. 1 of Japanese Laid-Open (Kokai) Utility Model Application No. 10605/80 shows an example in which this flexible tube structure is applied to a bending portion of an endoscope. More specifically, in the bending portion, the resilient thin plate is received in an internal space defined by the coil and extends in the longitudinal direction of the coil. Recesses are formed in each of opposite lateral edges of the resilient thin plate, and are juxtaposed in the longitudinal direction of this plate. The turn portions of the coil are engaged in the recesses. The bending portion is bent in a direction perpendicular to the plane of the resilient thin plate by an operating wire, so as to direct an inspection window and an illumination window of the rigid portion toward a desired direction.

The above resilient thin plate performs two functions. The first function is to prevent the coil from being axially compressed when pulling the operating wire, thereby ensuring a proper bending of the bending portion. The second function is to limit the direction of bending of the bending portion to a direction perpendicular to the plane of the resilient thin plate.

The above bending portion is simple in construction, and can be easily manufactured. However, since the resilient thin plate is received in the internal space of the coil In such a manner that this plate divides the internal space into two space portions, the resilient thin plate is obstructive when optical fiber bundles, guide tubes and etc., are to be inserted into the internal space. As a result, considerable limitations are imposed on the thicknesses or diameters of the optical fiber bundles and the guide tubes. Moreover, a dead space tends to be present in the two space portions, thus failing to make effective use of the internal space.

Referring to another prior art, Japanese Laid-Open Utility Model Application No. 110443/77 discloses a fiber scope including a bellows which is not designed to be bent by an operating wire.

SUMMARY OF THE INVENTION

It is a first object of this invention to provide a bending device which is simple in construction because of the use of a coil, and enables an internal space of the coil to be used effectively.

A second object of the invention is to provide a bending device which is simple in construction because of the use of a bellows, and can be bent by pulling an operating wire, and enables an internal space of the bellows to be used effectively.

The above first object has been achieved by a bending device comprising:
(a) a coil having an internal space therein, and comprising a number of turn portions juxtaposed in a direction of an axis of the coil;
(b) operating wire means for bending the coil, operating wire means having a proximal end portion adapted to receive an operating force, the operating wire means having a distal end portion substantially fixed to a distal end portion of the coil; and
(c) at least one pair of limitation members extending in an axial direction of the coil and mounted respectively on diametrically-opposite portions of the coil, the limitation members engaging the turn portions of the coil to keep the turn portions at substantially constant intervals, and the coil being bendable in a direction perpendicular to a plane in which the pair of limitation members are disposed.

The above second object has been achieved by a bending device comprising:
(a) a bellows having an internal space therein, and having a corrugated peripheral wall defined by first and second portions arranged alternately in a direction of an axis of the bellows, the first portions being bulged radially outwardly whereas the second portions are bulged radially inwardly;
(b) operating wire means for bending the bellows, the operating wire means having a proximal end portion adapted to receive an operating force, the operating wire means having a distal end portion substantially fixed to a distal end portion of the bellows; and
(c) at least one pair of independent limitation means for limiting an axial compression of the bellows, the pair of limitation means being arranged in an axial direction of the coil and mounted respectively on diametrically-opposite portions of the peripheral wall of the bellows, each of the pair of limitation means including insertion portions fitted respectively in at least one of the first portions and second portions of the bellows, and the bellows being bendable in a direction perpendicular to a plane in which the pair of limitation means are disposed.

DESCRIPTION OF THE PREFERRED EMBODIMENTS OF THE INVENTION

A preferred embodiment of the invention will now be described with reference to the drawings.

An endoscope shown in FIG. 1 comprises a hollow body an insertion portion 20 extending from a front end of the body 10, a bending portion (bending device) 30 extending from a distal end of the insertion portion 20, and a rigid portion 40 provided at a distal end of the bending portion 30. Each of the insertion portion 20 and the bending portion 30 has a tubular shape, and is so flexible as to be bent.

An ocular tube 11 is mounted on the proximal end of the body 10, and a manipulation dial 12 is mounted on the peripheral wall of the body 10, and a forceps inlet portion 13 is formed on the peripheral wall of the body 10. A cable (not shown) is fixedly secured at one end to the peripheral wail of the body 10, and a connector (not shown) to be connected to a light source device is mounted on the other end of this cable.

Figure 2:
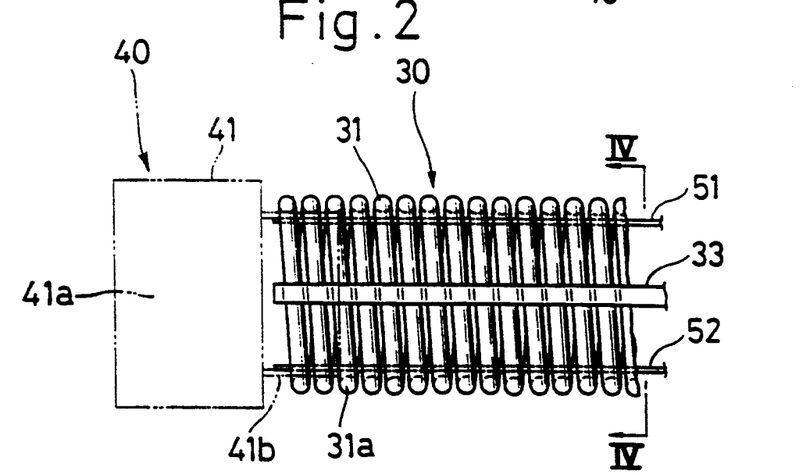
FIG. 2 is an enlarged, front-elevational view showing an internal structure of the bending portion.
Figure 3:
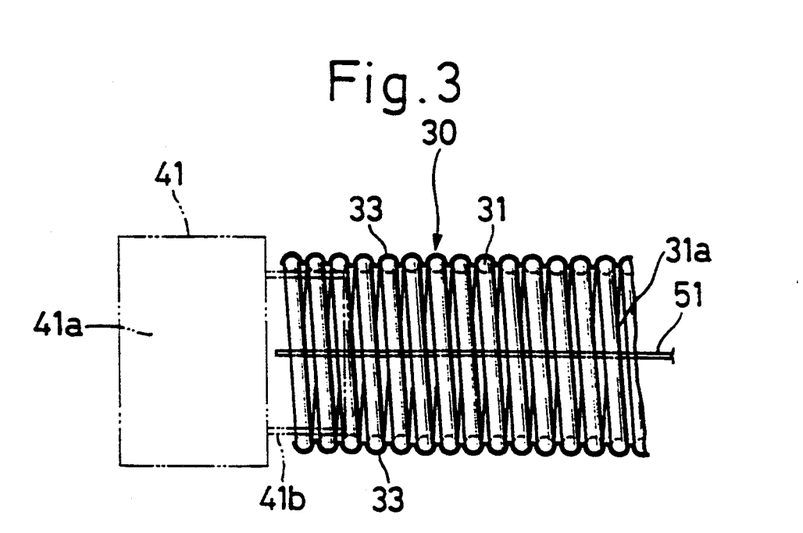
FIG. 3 is an enlarged, plan view showing the internal structure of the bending portion.

As shown in FIG. 2, the rigid portion 40 comprises a frame 41. The frame 41 has a base portion 41a of a circular cross-section, and a cylindrical portion 41b extending from the base portion 41a toward the bending portion 30. An inspection window, an illumination window, a forceps outlet and etc., are provided at the base portion 41a. The ocular tube 11 is optically connected to the inspection window via an image transmitting system (not shown) including an optical fiber bundle passing through the body 10, the insertion portion 20 and the bending portion 30. With this arrangement, inspection from the ocular tube 11 can be made. Illumination light from the light source device is applied to the illumination window via an optical fiber bundle passing through the above connector, the above cable, the body 10, the insertion portion 20 and the bending portion 30. The forceps outlet is connected to the forceps inlet portion 13 via a guide tube (not shown) passing through the body 10, the insertion portion 20 and the bending portion 30.

The insertion portion 20 includes a holder coil (not shown) made from a strip or elongated narrow plate. A proximal end of this holder coil is fixedly secured to the body 10, and the distal end of the holder coil is connected to a connecting tube (not shown). A braid tube (not shown) is fitted on the holder coil, and a tube 22 (shown only in FIG. 1) made of a resin or rubber is fitted on the braid tube.

Figure 4:
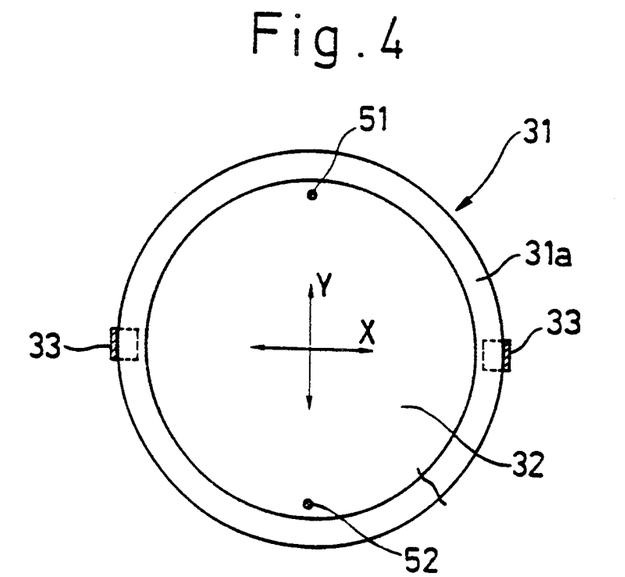
FIG. 4 is a cross-sectional view taken along the line IV—IV of FIG. 2.

The internal structure of the bending portion 30 will now be described in detail with reference to FIGS. 2 to 6. The bending portion 30 includes a coil 31. The coil 31 has a number of turn portions 31a each having a circular or round shape as viewed in the axial direction of the coil 31 as shown in FIG. 4. The turn portion 31a are juxtaposed in the axial direction of the coil 31. The proximal end of the coil 31 is fixedly secured to the above-mentioned connecting tube, and is connected to the distal end of the holder coil of the insertion portion 20 via this connecting tube. The distal end of the coil 31 is fixedly secured to the outer peripheral surface of the cylindrical portion 41b of the frame 41 of the rigid portion 40. The coil 31 has an internal space 32 therein, and the above-mentioned optical fiber bundles and guide tube are received in the internal space 32.

Figure 5:
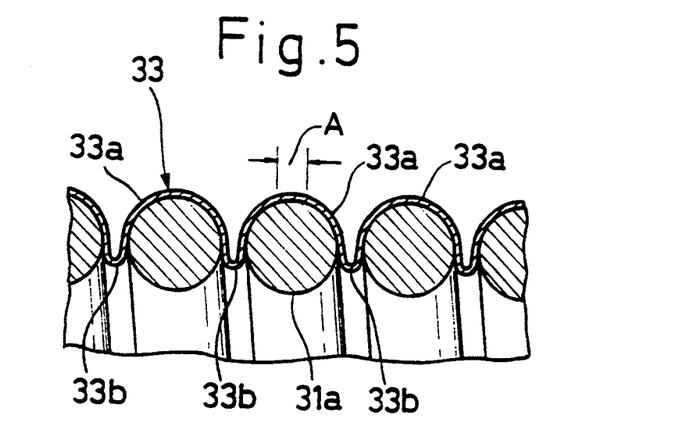
FIG. 5 is an enlarged, fragmentary view showing a condition of engagement between a coil and a strip.

A pair of strips or band-like plates (limiting members) 33 are mounted respectively on diametrically-opposite portions (i.e., portions diametrically opposite right and left in FIG. 4) of the outer periphery of the coil 31. Each Strip 33 is made of metal, and is relatively thin, and has a narrow width. Each strip 33 extends in the longitudinal direction of the coil 31 over the entire length thereof. As best shown in FIG. 5, the strip 33 is formed or bent into a corrugated shape, and has a number of support portions 33a of a generally semicircular cross-section spaced at equal intervals from one another along the length of the strip 33. The semi-circular support portion 33a has an inner diameter slightly greater than the transverse cross-section of the turn portion 31a of the coil 31. Each adjacent support portions 33a are interconnected by a connecting portion 33b. The outside section of each turn portion 31a of the coil 31 is received a respective one of the support portions 33a of each strip over about a half of the cross-section of the turn portion 31a. The support portions 33a of the strip 33 are fixedly secured respectively to the turn portions 31a of the coil by spot welding at regions indicated by reference character A in FIG. 5. With this construction, the turn portions 31a of the coil 31 are arranged at equal intervals in the axial direction of the coil 31. The strip plates 33 may be fixed to the coil 31 by an elastic adhesive or by brazing.

A braid tube, softer than the braid tube of the insertion portion 20, is fitted on the outer periphery of the coil and a tube 34 (only shown in FIG. 1), softer than the tube 22 of the insertion portion 20, is fitted on the outer periphery of this braid tube.

Next, a mechanism for bending the bending portion 30 will now be described. This mechanism includes two operating wires 51 and 52. The operating wires 51 and 52 are fixedly secured to a peripheral surface of a pulley 50 mounted within the body 10, and extend forwardly from the upper and lower portions of the pulley 50, respectively. The pulley 50 is connected to the manipulation dial 12 via a shaft (not shown) extending through the peripheral wall of the body 10.

in the insertion portion 20, the operating wires 51 and 52 are massed respectively through a pair of guide tubes of a small diameter. Each of these guide tubes is formed by spirally winding a wire, and is received within the holder coil. The proximal ends of the guide coils are fixedly secured respectively to diametrically-opposite portions of the body 10 (that is, opposed upper and lower portions of the body 10 in FIG. 1), and the distal ends of the guide coils are fixedly secured respectively to diametrically-opposite upper and lower portions of the inner peripheral surface of the above-mentioned connecting tube.

The operating wires 51 and 52 are passed through the internal space 32 of the coil 31, and are fixedly secured at their distal ends respectively to diametrically-opposite upper and lower portions (FIGS. 1 and 2) of the cylindrical portion 41b of the frame 41 of the rigid portion 40 by brazing. The positions of fixing of the distal ends of the operating wires 51 and 52, as well as the positions of fixing of the distal ends of the above guide coils, are circumferentially spaced 90° from the pair of strips 33.

The connecting portions 33b of the strips 33 have a relatively high rigidity to withstand a compressive force exerted in the longitudinal direction of the coil 31 upon pulling of the operating wire 51 or 52. Therefore, those sections of the turn portions 31a of the coil 31 engaged with each strip 33 are maintained at substantially constant intervals. As a result, the coil 31 and hence the bending portion 30 can not be bent in a direction X indicated in FIG. 4, and can be bent only in a direction Y in FIG. 4 (i.e., upward-downward direction in FIG. 1).

Figure 6:
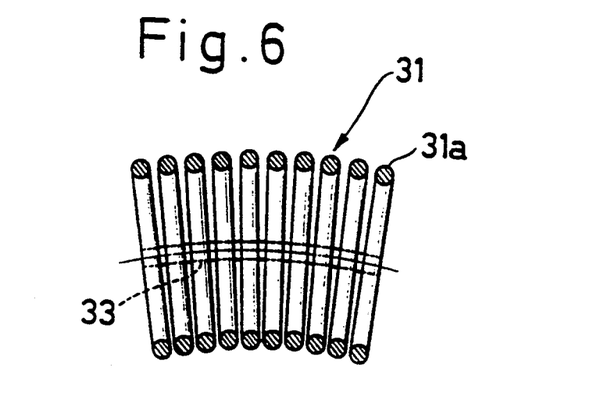
FIG. 6 is a cross-sectional view of portions of the coil and the strip in a bent condition of the bending portion.

In the above construction, when the manipulating dial 12 is angularly moved in a counterclockwise direction (FIG. 1), the operating wire 52 is pulled, and the operating wire 51 is loosened. At this time, since the axial compression of the coil 31 is limited by the strips 33, the pulling force applied by the operating wire 52 is effectively utilized to bend the coil 31 and hence the bending portion 30. More specifically, as shown in FIG. 6, the distance between those sections of the adjacent turn portions 31a engaged with each strip 33 remain unchanged, and the distance between the upper sections of the adjacent turn portions 31a increases whereas the distance between the lower sections of the adjacent turn portions 31a decreases. As a result, the bending portion 30 is bent downward.

In contrast, when the manipulating dial 12 is angularly moved in a clockwise direction, the operating wire 51 is pulled, and the operating wire 52 is loosened. As a result, the bending portion 30 is bent upward.

During the bending of the bending portion 30, the strips 33 will not affect or obstruct this bending. The reason for this is that because of the corrugated configuration of each strip 33, one lateral edge portion of the strip 33 is resiliently contracted whereas the other lateral edge portion is resiliently expanded, so that the strip 33 is bent in the direction of the width thereof, as shown in FIG. 6.

During the bending of the bending portion 30, the turn portions 31a of the coil 31 interfere with one another, thereby maintaining the cross-section of the bending portion 30 in a substantially circular shape. Also, the interference of the turn portions 31a with one another prevents the bending portion 30 from being bent only an one section thereof, thus ensuring a smooth bending.

In the above construction, the pair of strips 33 for limiting the coil 31 are independent of each other, and are not received in the internal space 32 of the coil 31. Therefore, the internal space 32 is not divided, and can be effectively used, without any dead space existing therein. As a result, limitations such as a limitation on the thickness of the optical fiber bundles are relaxed as compared with the above-mentioned conventional structure.

Other embodiments of the present invention will now be described. Those parts of these other embodiments corresponding respectively to those of the preceding embodiment are designated by identical reference numerals, respectively, and detailed explanation thereof will be omitted.

Figure 7:
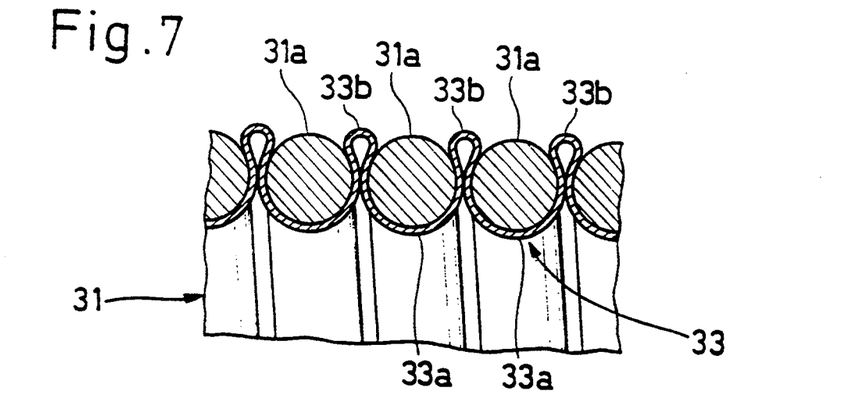
FIGS. 7 and 8 are views similar to FIG. 5, but showing modified bending portions, respectively.

In an embodiment shown in FIG. 7, each adjacent support portions 33a of each strip 33 are disposed in contact with each other, and adjacent turn portions 31a of a coil 31 are spaced from each other a distance twice the thickness of the strip 33. As a result, a pulling force applied by the operating wire is not partially absorbed by a resilient compression of the strips 33 in the axial direction of the coil 31, but is fully used to bend the bending portion.

In the embodiment of FIG. 7, connecting portions 33b of the strip 33 are projected considerably radially outwardly from an imaginary cylindrical surface in which the center of the transverse cross-sectional area of each turn portion 31a of the coil 31 lies. With this arrangement, the bending as shown in FIG. 6 is possible. Each of the strips 33 is disposed inside the coil 31, and the support portions 33a mainly support the inside sections of the turn portions 31a of the coil 31.

In the embodiment of FIG. 7, the turn portions 31a of the coil 31 are not fixed to the respective support portions 33a of each strip 33. In a natural condition of the strip 33 in which the strip is not subjected to any force, the inner diameter of the support portion 33a is slightly smaller than the diameter of the turn portion 31a, and the support portion 33a is kept engaged with (that is, held in intimate contact with) the turn portion 33a only by the resiliency of the support portion 33a. The support portion 33a circumferentially extends around the transverse cross-section of the turn portion 31a through an angle exceeding 180°. It is preferred that the opposite axial ends of each strip 33 be fixedly secured to the connecting tube at the distal end of the insertion portion and the cylindrical portion of the frame of the rigid portion, respectively.

Figure 8:
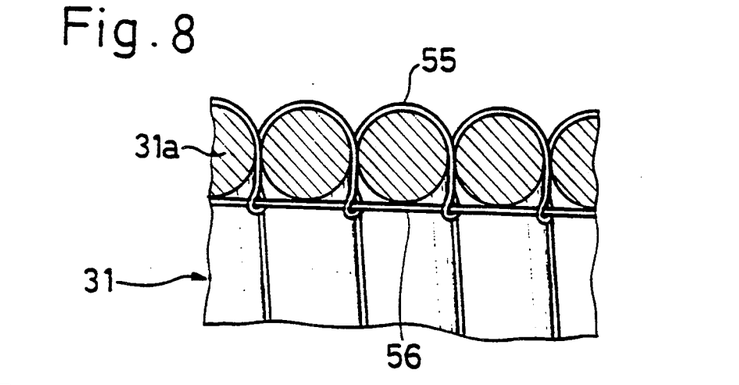

In an embodiment shown in FIG. 8, a pair of wires 55 of metal or a resin are used as limiting members. Each wire 55 cooperates with another wire 56, extending straight in an axial direction of a coil 31, to limit an axial compression of the coil 31. More specifically, the wire 55 is wound on about a half of an outer periphery of each turn portion 31a of the coil 31, and is folded or turned back around the wire 56, and further is wound on about a half of an outer periphery of the adjoining turn portion 31a. In this manner, the wire 55 is engaged with all the turn portions 31a in the axial direction of the coil 31. The distance between each adjacent turn portions 31a of the coil 31 is substantially equal to the diameter of the wire 55. One ends of the wires 55 and 56 are fixedly secured to the connecting tube at the distal end of the insertion portion, and the other ends of these wires are fixedly secured to the cylindrical portion of the frame of the rigid portion.

Figures 9, 10:
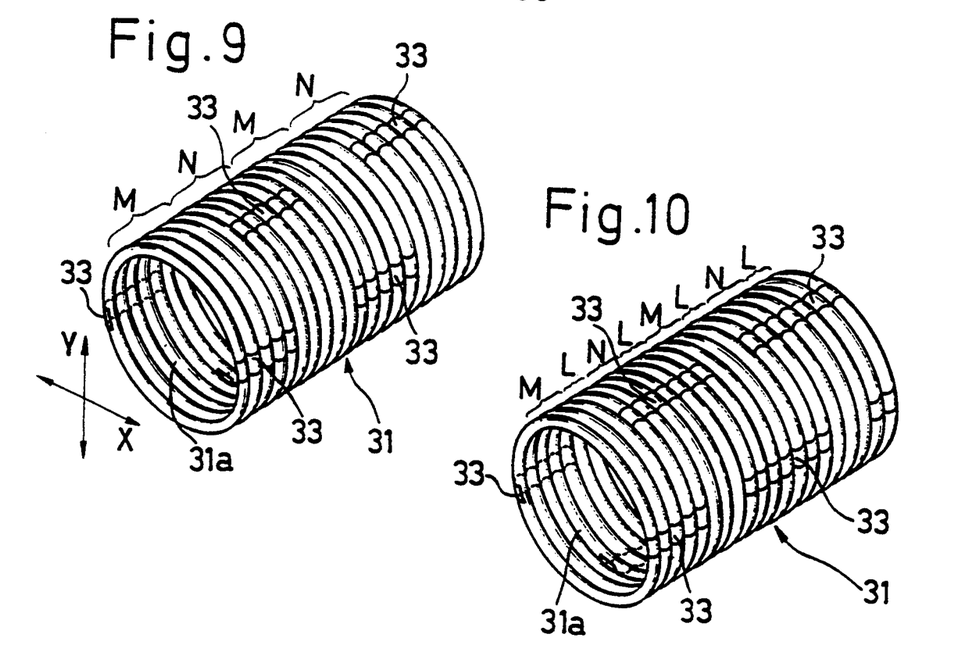
FIGS. 9 and 10 are perspective views showing internal structures of further modified bending portions, respectively.

In an embodiment shown in FIG. 9, a coil 31 can be bent in all directions. More specifically, the coil 31 is divided into alternate regions M and N in its axial direction. Each region includes, for example, five turn portions 31a. A pair of strips 33 are connected respectively to diametrically-opposite sections of the turn portions 31a of each region M which sections are spaced from each other in a direction X. Also, a pair of strips 33 are connected respectively to diametrically-opposite sections of the turn portions 31a of each region N which sections are spaced from each other in a direction Y. Four operating wires (not shown) are passed through an internal space of the coil 31. Two of the four operating wires are disposed in diametrically-opposite relation to each other in the direction X with respect to the coil 31 whereas the other two operating wires are disposed in diametrically-opposite relation to each other in the direction Y with respect to the coil 31. When one of the former two operating wires is pulled, the regions N of the coil 31 are bent in the direction X, with the regions M of the coil 31 hardly deformed. When one of the latter two operating wires is pulled, the regions M of the coil 31 are bent in the direction Y, with the regions N of the coil 31 hardly deformed. Thus, the coil 31 can be bent in four directions and hence all directions.

An embodiment shown in FIG. 10 is similar to the embodiment of FIG. 9, but differs therefrom on the following points. Namely, a coil 31 has regions L each interposed between adjacent regions M and N, the region L including two turn portions 31a. Two support portions 33a, provided at one end of each of two strips 33 extending from the region M, are engaged respectively with the two turn portions 31a defining the region L. Similarly, two support portions 33a, provided at one end of each of two strips 33 extending from the region N, are engaged respectively with the two turn portions 31a defining the region L. Thus, the two strips 33 extending from the region M and the two strips 33 extending from the region N are engaged with the two turn portions 31a (defining the region L) at four points spaced 90° from one another in the circumferential direction of the coil 31. Thus, the turn portions 31a of the region M and the turn portions 31a of the region N are interconnected via the turn portions 31a of the region L and the strips 33. This arrangement prevents a relative radial displacement between the turn portions 31a of the region M and the turn portions 31a of the region N when any of operating wires 51 to 54 is pulled.

Figure 11:
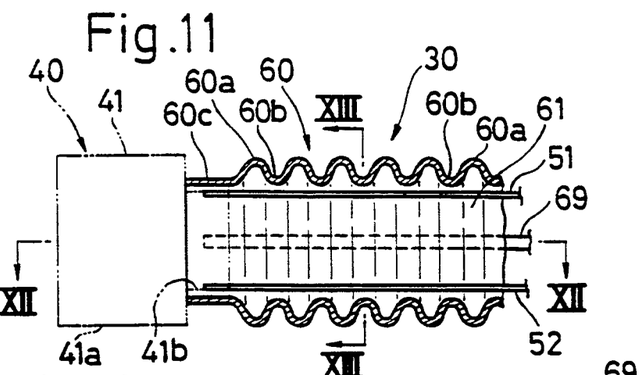
FIG. 11 is a cross-sectional view of a further modified bending portion.
Figure 12:
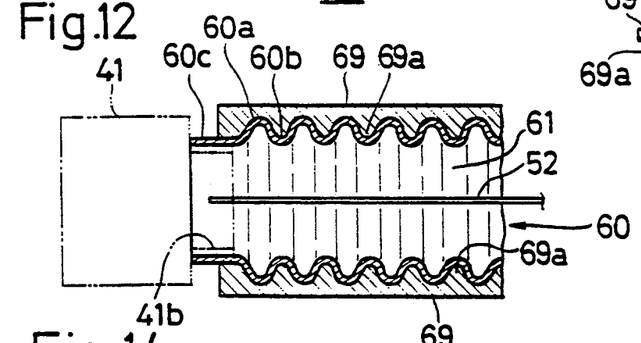
FIG. 12 is a cross-sectional view taken along the line XII—XII of FIG. 11.
Figure 13:
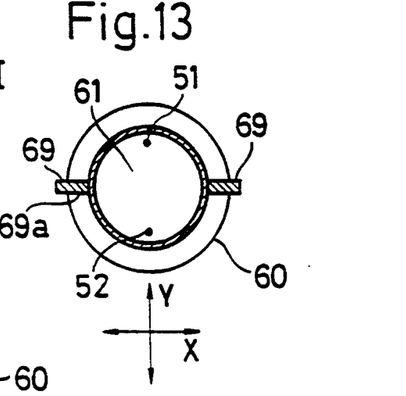
FIG. 13 is a cross-sectional view taken along the line XIII—XIII of FIG. 11.

In an embodiment shown in FIGS. 11 to 13, instead of the coil 31 used in the above embodiments, there is used a bellows 60 of metal which is thin and bendable, the bellows 60 being formed by an electroforming method. The bellows 60 is of a tubular shape having a circular transverse cross-section, and has an internal space 61 therein. The bellows 60 has first portions 60a radially outwardly bulged, and second portions 60b radially inwardly bulged. The first and second portions 60a and 60b are alternately arranged in the axial direction of the bellows 60, and the peripheral wall of the bellows 60 has a corrugated shape except for a distal end portion 60c and a proximal end portion of the bellows 60 which are cylindrical. The cylindrical distal end portion 60c is fitted on and fixedly secured to the cylindrical portion 41b of the frame 41 of the rigid portion 40. The cylindrical proximal end portion (not shown) of the bellows 60 is connected to the distal end of the holder coil of the insertion portion via the connecting tube.

A pair of limitation members 69 of metal each in the form of a strip or elongated plate are mounted respectively on diametrically-opposite portions of the outer periphery of the bellows 60 spaced from each other in a direction X, the pair of limitation members 69 extending in the axial direction of the bellows 60 over generally the entire length thereof. One lateral edges of the pair of limitation members 69 opposed to each other are of a corrugated shape corresponding to the corrugated shape of the outer peripheral surface of the bellows 60. This corrugated lateral edge of each of the limitation members 69 has a series of insertion portions (projections) 69a spaced at equal intervals from one another along the length of the limitation member 69. The insertion portions 69a are fitted respectively in the second portions 60b of the bellows 60, and the first portions 60a of the bellows 60 are fitted respectively in recesses each formed between each adjacent insertion portions 69a. Each of the limitation members 69 is fixedly secured by spot welding, an elastic adhesive, brazing or the like to the outer peripheral surface of the bellows 60 either at regions spaced along the length thereof or over the entire length thereof. The limitation members 69 limit the axial compression of the bellows 60, and allow the bellows 60 to be bent only in a direction Y perpendicular to a plane in which the limitation members 69 lie. Operating wires 51 and 52 are passed through the internal space 61 of the bellows 60, and are spaced 90° from the limitation members 69 in the circumferential direction of the bellows 60, and are disposed in diametrically opposite relation in the direction Y. A braid tube (not shown) is fitted around the bellows 60, and a tube is fitted around this braid tube. The use of such braid tube and such tube may be omitted.

In the above construction, when one of the operating wires 51 and 52 is pulled, one side of the bellows 60 along which the pulled operating wire is disposed is axially contracted whereas the other side of the bellows 60 disposed in diametrically opposite relation to the one side thereof is axially expanded. At this time, because the axial compression of the bellows 60 is limited by the limitation members 69, the overall length of the bellows 60 on the axis or centerline thereof is not changed. As a result, the bellows 60 is bent toward the side of the pulled operating wire. The purposes of the limitation members 69 are to positively convert the pulling force of the operating wire 51, 52 into a force for bending the bellows 60, and also to allow the bellows 60 to be bent in the intended direction.

Figure 14:
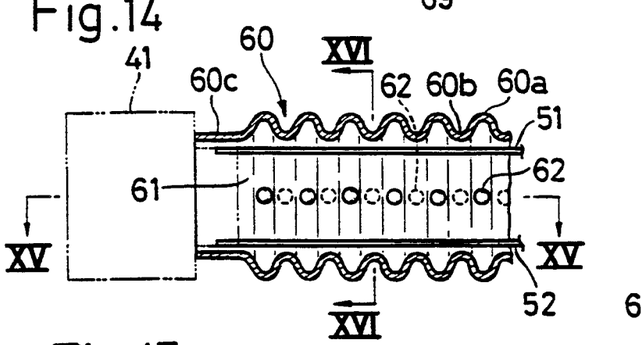
FIG. 14 is a view similar to FIG. 11, but showing a further modified form of the invention.
Figure 15:
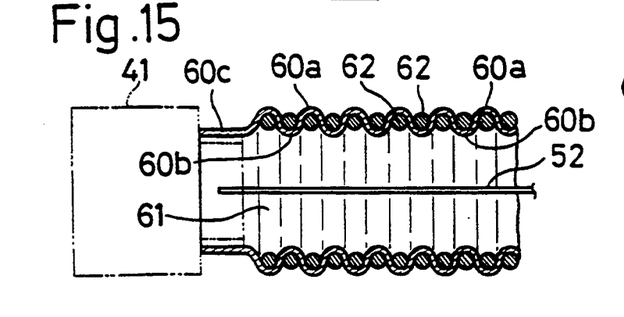
FIG. 15 is a cross-sectional view taken along the line XV—XV of FIG. 14.
Figure 16:
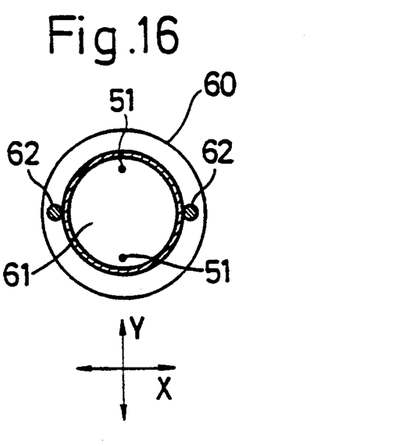
FIG. 16 is a cross-sectional view taken along the line XVI—XVI of FIG. 14.

An embodiment shown in FIGS. 14 to 16 is similar to the embodiment of FIGS. 11 to 13 in that a bellows 60 is used but differs therefrom in that spherical pieces 62 of metal (hereinafter referred to as "metal ball") are used as limitation means. Two rows of metal balls 62 are arranged over generally the entire length of the bellows 60, and more specifically are arranged respectively along two imaginary straight lines which extend parallel to the axis of the bellows 60 and are disposed respectively at diametrically-opposite portions of the corrugated peripheral wall of the bellows 60. The metal balls 62 in each row are disposed alternately inside and outside of the corrugated peripheral wall of the bellows 60. Those metal balls 62 disposed inside the bellows 60 are fitted in and fixedly secured to first portions 60a of the bellows 60, respectively, and those metal balls 62 disposed outside the bellows 60 are fitted in and fixedly secured to second portions 60b of the bellows 60. The metal balls 62 are fixedly secured to the bellows 60 by spot welding, an elastic adhesive, brazing or the like. The bellows 60 can not be axially expanded or contracted at those portions thereof to which the metal balls 62 are secured, and can be axially expanded or contracted only at those portions thereof where the metal balls 62 are not attached. As a result, the bellows 60 can not be bent in a direction X (FIG. 16), and can be bent only in a direction Y perpendicular to a plane in which the two rows of metal balls 62 are disposed.

Each row of metal balls 62 are disposed between a cylindrical surface inscribed in the bellows 60 and a cylindrical surface circumscribed about the bellows 60, and therefore the use of the metal balls 62 does not increase the diameter of the bending portion.

Figure 17:
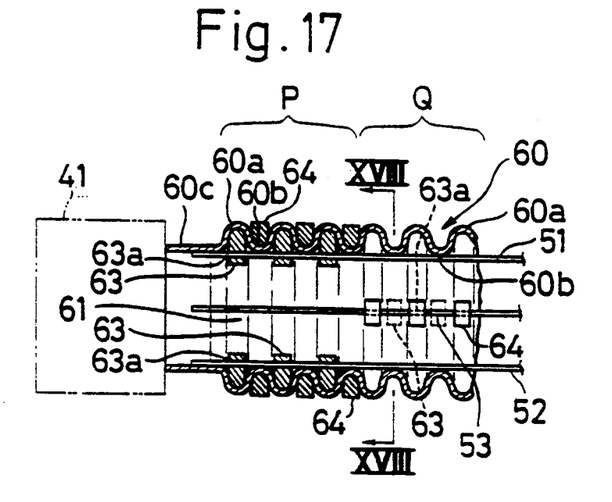
FIG. 17 is a view similar to FIG. 11, but showing a further modified form of the invention.
Figure 18:
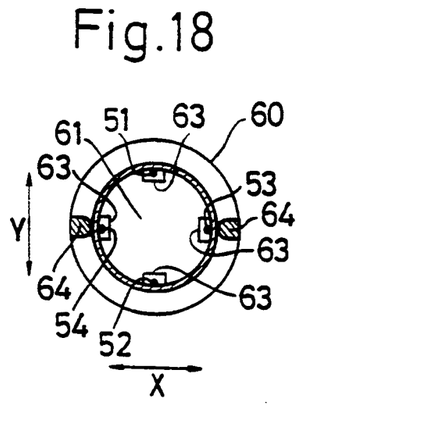
FIG. 18 is a cross-sectional view taken along the line XVIII—XVIII of FIG. 17.

An embodiment shown in FIGS. 17 and 18 is similar to the embodiments of FIGS. 11 to 16 in that a bellows is used, but differs therefrom in that the bellows can be bent in all directions. More specifically, the bellows 60 has regions P and Q arranged alternately in the axial direction of the bellows 60. At each of the regions P, two rows of alternate first and second pieces 63 and 64 are arranged respectively along two imaginary straight lines which extend parallel to the axis of the bellows 60 and are disposed respectively at diametrically-opposite portions of the corrugated peripheral wall of the bellows 60 spaced from each other in a direction Y. At each of the regions Q, two rows of alternate first and second pieces 63 and 64 are arranged respectively along two imaginary straight lines which extend parallel to the axis of the bellows 60 and are disposed respectively at diametrically-opposite portions of the corrugated peripheral wall of the bellows 60 spaced from each other in a direction X.

Each of the pieces 63 and 64 has one end portion which is rounded or semi-spherical, and the other end portion has a rectangular cross-section. The first piece 63 is longer than the second piece 64.

The first pieces 63 are disposed inside the corrugated peripheral wall of the bellows 60, and their rounded one end portions are fitted in and fixedly secured to first portions 60a of the bellows 60, respectively. The other end portions of the first pieces 63 are projected radially inwardly beyond the inner peripheries of second portions 60b of the bellows 60. An insertion hole 63a is formed through each of these projected end portions, and extends in the axial direction of the bellows 60. The second pieces 64 are disposed outside the corrugated peripheral wall of the bellows 60, and their rounded one end portions are fitted in and fixedly secured to the second portions 60b of the bellows 60. The other ends of the second pieces 64 either coincide with a circumscribed cylindrical surface of the bellows 60 or disposed radially inwardly of this circumscribed cylindrical surface.

Four operating wires 51 to 54 are disposed in an internal space 61 of the bellows 60, and are passed through the insertion holes 63a of the four rows of first pieces 63, respectively.

In the above construction, when one of the operating wires 51 and 52 is pulled, the bellows 60 can not be bent at the regions P, but can be bent at the regions Q in the direction Y (FIG. 18). When one of the operating wires 53 and 54 is pulled, the bellows 60 can not be bent at the regions Q, but can be bent at the regions P in the direction X (FIG. 18). Thus, the bellows 60 can be bent in all directions.

In this embodiment, since the operating wires 51 to 54 are guided by the first pieces 63, the optical fibers, the guide tubes and etc., received in the internal space 61 of the bellows 60 are not pressed by the operating wires when the bellows 60 is bent.

Figure 19:
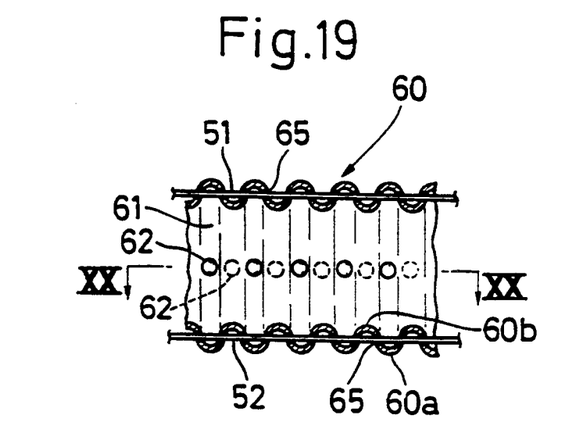
FIG. 19 is a view similar to FIG. 11, but showing a further modified form of the invention.
Figure 20:
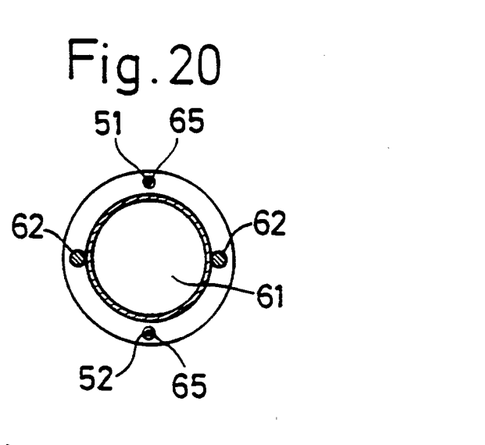
FIG. 20 is a cross-sectional view taken along the line XX—XX of FIG. 19.

An embodiment shown in FIGS. 19 and 20 is similar to the embodiment of FIGS. 14 to 16, but differs therefrom on the following points. Two rows of insertion holes 65 are formed respectively through diametrically-opposite portions of corrugations of a peripheral wall of a bellows 60, the two rows of insertion holes 65 being disposed respectively on two straight lines parallel to the axis of the bellows 60. Operating wires 51 and 52 are passed through the two rows of insertion holes 65, respectively.

Figure 21:
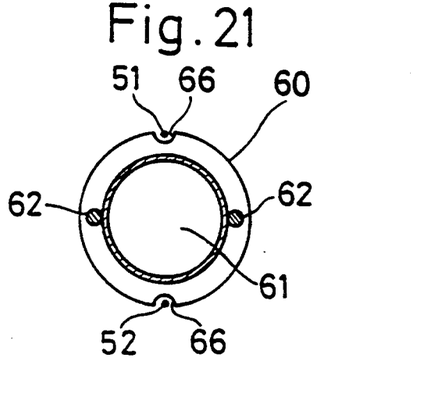
FIG. 21 is a view similar to FIG. 20, but showing a further modified form of the invention.

In an embodiment shown in FIG. 21, two rows of notches 66 are formed respectively in diametrically-opposite sections of outer peripheries of first portions 60a of a bellows 60, the two rows of notches 66 being disposed respectively on two straight lines parallel to the axis of the bellows 60. Operating wires 51 and 52 are received in the two rows of notches 66, respectively.

In the embodiments shown in FIGS. 19 and 20 and FIG. 21, since the operating wires 51 and 52 are not disposed in an internal space 61 of the bellows 60, the internal space 61 offers a greater area or space used for receiving the associated parts such as optical fibers. And besides, since the operating wires 51 and 52 are not moved into the internal space 61 when the bellows 60 is bent, the optical fibers, the guide tubes and etc., are not pressed by the operating wires.

The present invention is not to be restricted to the above embodiments, and various modifications can be made.

For example, the limitation members 61 and the pieces 62 to 64 may be made of an elastic material such as relatively rigid rubber.

The use of only one operating wire is possible, in which case the bending portion can be bent in one direction.

The present invention can be applied to the endoscope of the type in which the thicknesses or diameters of the insertion portion and the bending portion are very small, and further the present invention can be applied to a medical catheter.

What is claimed is:

1. A bending device comprising:
   (a) a bellows having an internal space therein, and having a corrugated peripheral wall defined by first and second portions arranged alternately in a direction of an axis of said bellows, said first portions being bulged radially outwardly whereas said second portions are bulged radially inwardly;
   (b) means for bending said bellows comprising a wire, said means for bending having a proximal end portion adapted to receive a force, said means for bending having a distal end portion substantially fixed to a distal end portion of said bellows; and
   (c) at least one pair of independent limitation means for limiting an axial compression of said bellows, said pair of limitation means being arranged in an axial direction of said bellows and mounted respectively on diametrically-opposite portions of said peripheral wall of said bellows, each of said pair of limitation means including insertion portions fitted respectively in at least one of said first portions and second portions of said bellows, and said bellows being bendable in a direction perpendicular to a plane in which said pair of limitation means are disposed.

2. A bending device according to claim 1, in which said pair of limitation means extend over generally an entire length of said bellows, and are disposed in a common plane.

3. A bending device according to claim 1, in which each of said pair of limitation means comprises a limitation member extending in the axial direction of said bellows, said limitation member being disposed outside said peripheral wall of said bellows in such a manner that said insertion portions are fitted respectively in said second portions of said bellows.

* * * * *